(12) United States Patent
Miller et al.

(10) Patent No.: US 9,695,098 B2
(45) Date of Patent: Jul. 4, 2017

(54) HYDROFORMYLATION PROCESS

(71) Applicant: Dow Technology Investments LLC, Midland, MI (US)

(72) Inventors: Glenn A. Miller, South Charleston, WV (US); Jason F. Giles, Missouri City, TX (US); Irvin B. Cox, The Villages, FL (US)

(73) Assignee: DOW TECHNOLOGY INVESTMENTS LLC, Midland, MI (US)

( * ) Notice: Subject to any disclaimer, the term of this patent is extended or adjusted under 35 U.S.C. 154(b) by 0 days.

(21) Appl. No.: 15/032,322

(22) PCT Filed: Dec. 9, 2014

(86) PCT No.: PCT/US2014/069315
§ 371 (c)(1),
(2) Date: Apr. 27, 2016

(87) PCT Pub. No.: WO2015/094813
PCT Pub. Date: Jun. 25, 2015

(65) Prior Publication Data
US 2016/0257636 A1    Sep. 8, 2016

Related U.S. Application Data

(60) Provisional application No. 61/918,344, filed on Dec. 19, 2013.

(51) Int. Cl.
| | | |
|---|---|---|
| *C07C 45/50* | (2006.01) | |
| *B01J 31/24* | (2006.01) | |
| *C07C 45/78* | (2006.01) | |

(52) U.S. Cl.
CPC ............. *C07C 45/50* (2013.01); *B01J 31/24* (2013.01); *C07C 45/78* (2013.01); *B01J 2231/321* (2013.01); *B01J 2531/822* (2013.01)

(58) Field of Classification Search
CPC ...................................................... C07C 45/50
USPC ........................................................ 568/454
See application file for complete search history.

(56) References Cited

U.S. PATENT DOCUMENTS

| | | |
|---|---|---|
| 3,415,906 A | 12/1968 | Shepard et al. |
| 3,527,809 A | 9/1970 | Pruett et al. |
| 4,148,830 A | 4/1979 | Pruett et al. |
| 4,166,773 A | 9/1979 | Higley et al. |
| 4,247,486 A | 1/1981 | Brewester et al. |
| 4,277,627 A | 7/1981 | Bryant et al. |
| 4,329,507 A | 5/1982 | Takeda et al. |
| 4,518,809 A | 5/1985 | Forster et al. |
| 4,528,403 A | 7/1985 | Tano et al. |
| 4,567,302 A | 1/1986 | Sivaramakrishnan |
| 4,567,306 A | 1/1986 | Dennis et al. |
| 4,593,127 A * | 6/1986 | Bunning ............... C07C 45/50  568/454 |
| 4,599,206 A | 7/1986 | Billig et al. |
| 4,668,651 A | 5/1987 | Billig et al. |
| 4,717,775 A | 1/1988 | Billig et al. |
| 4,748,261 A | 5/1988 | Billig et al. |
| 4,769,498 A | 9/1988 | Billig et al. |
| 4,774,361 A | 9/1988 | Maher et al. |
| 4,828,042 A | 5/1989 | Arnold |
| 4,835,299 A | 5/1989 | Maher et al. |
| 4,885,401 A | 12/1989 | Billig et al. |
| 5,001,274 A | 3/1991 | Bunning |
| 5,087,763 A | 2/1992 | Sorensen |
| 5,102,505 A | 4/1992 | Sorensen |
| 5,105,018 A | 4/1992 | Miyazawa et al. |
| 5,110,990 A | 5/1992 | Blessing et al. |
| 5,113,022 A | 5/1992 | Abatjoglou et al. |
| 5,179,055 A | 1/1993 | Wink et al. |
| 5,202,297 A | 4/1993 | Lorz et al. |
| 5,235,113 A | 8/1993 | Sato et al. |
| 5,254,741 A | 10/1993 | Lorz et al. |
| 5,264,616 A | 11/1993 | Roeper et al. |
| 5,277,532 A | 1/1994 | Pazzaglia |
| 5,288,918 A | 2/1994 | Maher et al. |
| 5,312,996 A | 5/1994 | Packett |
| 5,360,938 A | 11/1994 | Babin et al. |
| 5,364,950 A | 11/1994 | Babin et al. |
| 5,367,106 A * | 11/1994 | Unruh .................... C07C 45/50  568/453 |
| 5,391,801 A | 2/1995 | Sato et al. |
| 5,430,194 A | 7/1995 | Barner et al. |
| 5,463,137 A | 10/1995 | Ramachandran et al. |
| 5,491,266 A | 2/1996 | Babin et al. |
| 5,527,950 A | 6/1996 | Hansen et al. |
| 5,648,554 A | 7/1997 | Mori et al. |
| 5,675,041 A | 10/1997 | Kiss et al. |
| 5,681,473 A | 10/1997 | Miller et al. |

(Continued)

FOREIGN PATENT DOCUMENTS

| | | |
|---|---|---|
| CN | 101293818 A | 10/2008 |
| CN | 101565353 A | 10/2009 |

(Continued)

OTHER PUBLICATIONS

Lide, David, CRC Handbook of Chemistry and Physics, (1991-1992) 72nd Ed. p. I-10, CRC Press.
PCT/US2014/069315, International Search Report and Written Opinion mailed Feb. 25, 2015.
PCT/US2014/069315, International Preliminary Report on Patentability issued Jun. 21, 2016.

*Primary Examiner* — Sikarl Witherspoon

(57) ABSTRACT

A multi-reactor hydroformylation process wherein a common product-catalyst separation zone is employed.

15 Claims, 3 Drawing Sheets

(56) References Cited

U.S. PATENT DOCUMENTS

| | | |
|---|---|---|
| 5,710,344 A | 1/1998 | Breikss et al. |
| 5,728,893 A | 3/1998 | Becker et al. |
| 5,731,472 A | 3/1998 | Leung et al. |
| 5,731,473 A | 3/1998 | Bryant et al. |
| 5,741,942 A | 4/1998 | Bryant et al. |
| 5,741,944 A | 4/1998 | Bryant et al. |
| 5,744,649 A | 4/1998 | Bryant et al. |
| 5,789,625 A | 8/1998 | Bryant et al. |
| 5,929,289 A | 7/1999 | Abatjoglou et al. |
| 5,952,530 A | 9/1999 | Argyropoulos et al. |
| 6,265,620 B1 | 7/2001 | Urata et al. |
| 6,440,891 B1 | 8/2002 | Maas et al. |
| 6,482,992 B2 * | 11/2002 | Scholz .................. C07C 29/16 568/451 |
| 6,846,960 B2 | 1/2005 | Tolleson et al. |
| 6,969,777 B2 * | 11/2005 | Walz ...................... C07C 45/50 568/451 |
| 6,995,292 B2 | 2/2006 | Tolleson et al. |
| 7,009,068 B2 | 3/2006 | Schmutzler et al. |
| 7,145,042 B2 | 12/2006 | Volland et al. |
| 7,196,230 B2 | 3/2007 | Peng et al. |
| 7,262,330 B2 | 8/2007 | Ueda et al. |
| 7,405,329 B2 * | 7/2008 | Beadle ................... C07C 45/50 568/451 |
| 7,586,010 B2 | 9/2009 | Liu et al. |
| 7,615,645 B2 | 11/2009 | Volland et al. |
| 7,674,937 B2 | 3/2010 | Tolleson et al. |
| 7,872,156 B2 | 1/2011 | Liu et al. |
| 8,003,816 B2 | 8/2011 | Selent et al. |
| 8,134,031 B2 | 3/2012 | Peng |
| 8,598,390 B2 | 12/2013 | Eisenschmid et al. |
| 8,791,304 B2 | 7/2014 | Ko et al. |
| 8,884,072 B2 | 11/2014 | Miller et al. |

FOREIGN PATENT DOCUMENTS

| | | |
|---|---|---|
| CN | 102826969 A | 12/2012 |
| CN | 102826973 A | 12/2012 |
| CN | 103130623 A | 6/2013 |
| GB | 1387657 A | 3/1975 |
| JP | 2006/306815 A | 11/2006 |
| JP | 3864668 B2 | 1/2007 |

\* cited by examiner

HYDROFORMYLATION PROCESS

BACKGROUND OF THE INVENTION

The invention relates to a process for the hydroformylation of olefins to produce aldehydes.

A number of hydroformylation processes involve the further processing of vent streams from hydroformylation reactors. The purpose of the vent streams is to prevent the accumulation of inert impurities, such as $N_2$, $CO_2$, Ar, $CH_4$ and hydrocarbons, by purging them from the process. The inerts may get into the process as impurities in the feeds. These are generally vented prior to the product-catalyst separation zone to reduce the load on the separation systems. Unfortunately, venting these inerts also tends to lose valuable reactants, such as olefin.

There have been a number of disclosures teaching how to recover and recycle the olefin contained in these vents. Examples of these vent reactor processes are disclosed in GB 1,387,657 and U.S. Pat. Nos. 4,593,127, 5,105,018, 5,367,106, 5,675,041, 6,482,992, 6,969,777 and 7,405,329. Each process has a product-catalyst separation zone for each reactor system. In several cases, the product-catalyst separation step is performed in the hydroformylation reactor vessel in a so-called "gas-recycle" system as described in U.S. Pat. No. 4,247,486.

U.S. Pat. No. 5,367,106 teaches sending the reactor vent stream sent to a second, plug flow reactor. There are effectively two product-catalyst separation zones in this complex scheme, the first being in the primary reactor and the second being a pair of flashpots off of the plug flow reactor.

CN 102826973 teaches sending the liquid output of the first reactor to a syngas stripper to remove the olefin prior to the product-catalyst separation zone. The effluent streams of all the reactors feed into the syngas stripper prior to entering the product-catalyst separation zone. The process discards the final reactor vent as well as the vent from the vaporizer, which may contain substantial amounts of unreacted olefin. It is known from U.S. Pat. Nos. 4,277,627 and 5,675,041 that exposure of catalyst solution to high levels of syngas can degrade catalyst life. It is not economical to send catalyst-containing streams containing some of the most common hydroformylation ligands, such as triphenylphosphine, to the syngas stripper, since at the bottom of the stripping column the catalyst will be exposed to elevated CO partial pressure and elevated temperature in the absence of olefin, thereby causing catalyst deactivation.

CN 103130623 discloses a process that uses a compressor to pressurize the vent stream from the first reactor into a second reactor. The combined output of both reactors is sent to a syngas stripper before product-catalyst separation.

CN 101293818 shows a flowsheet wherein the each reactor has a distillation unit wherein unreacted olefin is removed. In order to efficiently remove the olefin from the first reactor effluent, this distillation involves a substantial capital investment. The combined output of the reactors is then sent to a product-catalyst separation zone. The use of multiple vaporizers means repeated exposure of the catalyst to harsh conditions which promote ligand and/or catalyst degradation and heavies formation.

The above schemes involve complex, expensive designs. It would be desirable to have a hydroformylation process capable of maintaining high olefin conversion, but at lower capital cost. It would also be desirable to have an improved process that is more compact, with lower catalyst requirements.

SUMMARY OF THE INVENTION

The invention is such a process comprising
(a) contacting in a primary reactor CO, $H_2$, and a feed stream comprising an olefin in the presence of a hydroformylation catalyst in a reaction fluid under hydroformylation conditions sufficient to form at least one aldehyde product;
(b) passing a liquid effluent stream from the primary reactor to a product-catalyst separation zone,
(c) removing from the product-catalyst separation zone a crude product stream and a liquid catalyst recycle stream;
(d) then, separating the crude product stream into a vent stream and an unrefined product stream;
(e) passing the vent stream, which comprises an olefin, to a secondary reactor;
(f) contacting in the secondary reactor CO, $H_2$, and the olefin of the vent stream in the presence of a hydroformylation catalyst in a reaction fluid under hydroformylation conditions sufficient to form at least one aldehyde product;
(g) passing a liquid effluent stream from the secondary reactor to the product-catalyst separation zone.

Surprisingly, the recycle of the vent stream does not result in hydrocarbon accumulation in the process.

DETAILED DESCRIPTION OF THE INVENTION

Figure 1:
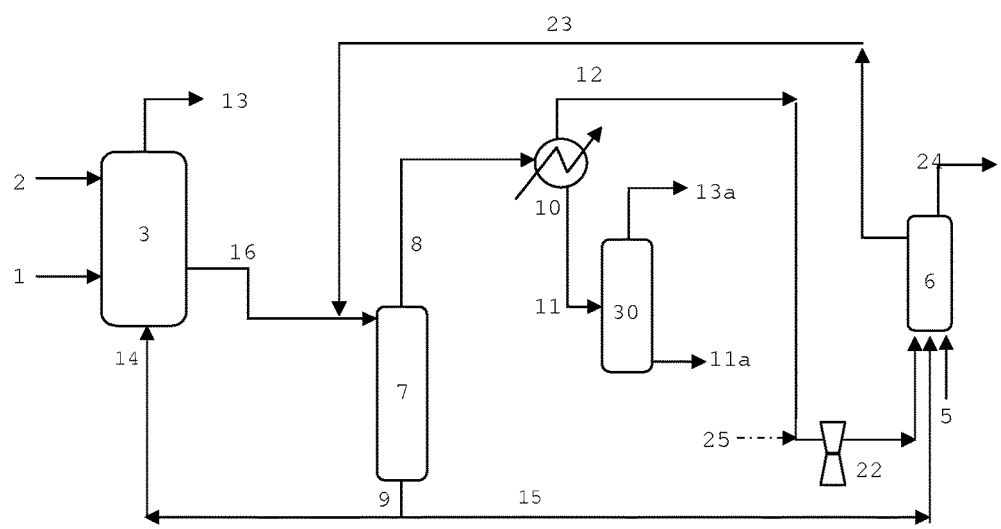
FIG. 1 is a schematic of an hydroformylation process that employs a common product-catalyst separation zone, e.g. a vaporizer.

The disclosed process comprises contacting CO, $H_2$, and at least one olefin under hydroformylation conditions sufficient to form at least one aldehyde product in the presence of a catalyst comprising, as components, a transition metal and an organophosphorous ligand.

All references to the Periodic Table of the Elements and the various groups therein are to the version published in the CRC Handbook of Chemistry and Physics, 72nd Ed. (1991-1992) CRC Press, at page I-10.

Unless stated to the contrary, or implicit from the context, all parts and percentages are based on weight and all test methods are current as of the filing date of this application. For purposes of United States patent practice, the contents of any referenced patent, patent application or publication are incorporated by reference in their entirety (or its equivalent US version is so incorporated by reference) especially with respect to the disclosure of definitions (to the extent not inconsistent with any definitions specifically provided in this disclosure) and general knowledge in the art.

As used herein, "a," "an," "the," "at least one," and "one or more" are used interchangeably. The terms "comprises," "includes," and variations thereof do not have a limiting meaning where these terms appear in the description and claims. Thus, for example, an aqueous composition that includes particles of "a" hydrophobic polymer can be interpreted to mean that the composition includes particles of "one or more" hydrophobic polymers.

Also herein, the recitations of numerical ranges by endpoints include all numbers subsumed in that range (e.g., 1 to 5 includes 1, 1.5, 2, 2.75, 3, 3.80, 4, 5, etc.). For the purposes of the invention, it is to be understood, consistent with what one of ordinary skill in the art would understand, that a numerical range is intended to include and support all possible subranges that are included in that range. For example, the range from 1 to 100 is intended to convey from 1.01 to 100, from 1 to 99.99, from 1.01 to 99.99, from 40 to 60, from 1 to 55, etc. Also herein, the recitations of numerical ranges and/or numerical values, including such recitations in the claims, can be read to include the term "about." In such instances the term "about" refers to numerical ranges and/or numerical values that are substantially the same as those recited herein.

As used herein, the term "ppmw" means part per million by weight.

For purposes of this invention, the term "hydrocarbon" is contemplated to include all permissible compounds having at least one hydrogen and one carbon atom. Such permissible compounds may also have one or more heteroatoms. In a broad aspect, the permissible hydrocarbons include acyclic (with or without heteroatoms) and cyclic, branched and unbranched, carbocyclic and heterocyclic, aromatic and nonaromatic organic compounds which can be substituted or unsubstituted.

As used herein, the term "substituted" is contemplated to include all permissible substituents of organic compounds unless otherwise indicated. In a broad aspect, the permissible substituents include acyclic and cyclic, branched and unbranched, carbocyclic and heterocyclic, aromatic and nonaromatic substituents of organic compounds. Illustrative substituents include, for example, alkyl, alkyloxy, aryl, aryloxy, hydroxyalkyl, aminoalkyl, in which the number of carbons can range from 1 to 20 or more, preferably from 1 to 12, as well as hydroxy, halo, and amino. The permissible substituents can be one or more and the same or different for appropriate organic compounds. This invention is not intended to be limited in any manner by the permissible substituents of organic compounds.

As used herein, the term "hydroformylation" is contemplated to include, but is not limited to, all hydroformylation processes that involve converting one or more substituted or unsubstituted olefinic compounds or a reaction mixture comprising one or more substituted or unsubstituted olefinic compounds to one or more substituted or unsubstituted aldehydes or a reaction mixture comprising one or more substituted or unsubstituted aldehydes. The aldehydes may be asymmetric or non-asymmetric.

The terms "reaction fluid," "reaction medium" and "catalyst solution" are used interchangeably herein, and may include, but are not limited to, a mixture comprising: (a) a metal-organophosphorous ligand complex catalyst, (b) free organophosphorous ligand, (c) aldehyde product formed in the reaction, (d) unreacted reactants, (e) a solvent for said metal-organophosphorous ligand complex catalyst and said free organophosphorous ligand, and, optionally, (f) one or more phosphorus acidic compounds formed in the reaction (which may be homogeneous or heterogeneous, and these compounds include those adhered to process equipment surfaces). The reaction fluid can encompass, but is not limited to, (a) a fluid in a reactor, (b) a fluid stream on its way to a separation zone, (c) a fluid in a separation zone, (d) a recycle stream, (e) a fluid withdrawn from a reaction zone or separation zone, (f) a withdrawn fluid being treated with an aqueous buffer solution, (g) a treated fluid returned to a reaction zone or separation zone, (h) a fluid in an external cooler, and (i) ligand decomposition products and their salts.

"Hydrolyzable phosphorous ligands" are trivalent phosphorous ligands that contain at least one P—Z bond wherein Z is oxygen, nitrogen, chlorine, fluorine or bromine Examples include, but are not limited to, phosphites, phosphino-phosphites, bisphosphites, phosphonites, bisphosphonites, phosphinites, phosphoramidites, phosphino-phosphoramidites, bisphosphoramidites, fluorophosphites, and the like. The ligands may include chelate structures and/or may contain multiple P—Z moieties such as polyphosphites, polyphosphoramidites, etc. and mixed P—Z moieties such as phosphite-phosphoramidites, flurophosphite-phosphites, and the like.

The term "free ligand" means ligand that is not complexed with (tied to or bound to) the metal, e.g., metal atom, of the complex catalyst.

Hydrogen and carbon monoxide are required for the process. These may be obtained from any suitable source, including petroleum cracking and refinery operations. Syngas mixtures are preferred as a source of hydrogen and CO.

Syngas (from synthesis gas) is the name given to a gas mixture that contains varying amounts of CO and $H_2$. Production methods are well known and include, for example: (1) steam reforming and partial oxidation of natural gas or liquid hydrocarbons; and (2) the gasification of coal and/or biomass. Hydrogen and CO typically are the main components of syngas, but syngas may contain carbon dioxide and inert gases such as $N_2$ and Ar. The molar ratio of $H_2$ to CO varies greatly but generally ranges from 1:100 to 100:1 and preferably between 1:10 and 10:1. Syngas is commercially available and is often used as a fuel source or as an intermediate for the production of other chemicals. The most preferred $H_2$:CO molar ratio for chemical production is between 3:1 and 1:3 and usually is targeted to be between about 1:2 and 2:1 for most hydroformylation applications.

The substituted or unsubstituted olefinic unsaturated starting material reactants that may be employed in the hydroformylation process include both optically active (prochiral and chiral) and non-optically active (achiral) olefinic unsaturated compounds containing from 2 to 40, preferably 3 to 20, carbon atoms. Such olefinic unsaturated compounds can be terminally or internally unsaturated and be of straight-chain, branched chain or cyclic structures, as well as olefin mixtures, such as obtained from the oligomerization of propene, butene, isobutene, etc. (such as so called dimeric, trimeric or tetrameric propylene and the like, as disclosed, for example, in U.S. Pat. Nos. 4,518,809 and 4,528,403). Moreover, such olefin compounds may further contain one or more additional ethylenic unsaturated groups, and mixtures of two or more different olefinic unsaturated compounds may be employed as the starting hydroformylation material if desired. For example, commercial alpha olefins containing four or more carbon atoms may contain minor amounts of corresponding internal olefins and/or their corresponding saturated hydrocarbon and that such commercial olefins need not necessarily be purified from same prior to being hydroformylated. Illustrative mixtures of olefinic starting materials that can be employed in the hydroformylation reactions include, for example, mixed butenes, e.g., Raffinate I and II. Further such olefinic unsaturated compounds and the corresponding aldehyde products derived therefrom may also contain one or more groups or substituents which do not unduly adversely affect the hydroformylation process or the process of this invention such as described, for example, in U.S. Pat. Nos. 3,527,809, 4,769,498 and the like.

Most preferably, the invention is especially useful for the production of non-optically active aldehydes, by hydroformylating achiral alpha-olefins containing from 2 to 30, preferably 3 to 20, carbon atoms, and achiral internal olefins containing from 4 to 20 carbon atoms as well as starting material mixtures of such alpha olefins and internal olefins.

Illustrative alpha and internal olefins include, for example, ethylene, propylene, 1-butene, 1-pentene, 1-hexene, 1-octene, 1-nonene, 1-decene, 1-undecene, 1-dodecene, 1-tridecene, 1-tetradecene, 1-pentadecene, 1-hexadecene, 1-heptadecene, 1-octadecene, 1-nonadecene, 1-eicosene, 2-butene, 2-methyl propene (isobutylene), 2-methylbutene, 2-pentene, 2-hexene, 3-hexane, 2-heptene, 2-octene, cyclohexene, propylene dimers, propylene trimers, propylene tetramers, butadiene, piperylene, isoprene, 2-ethyl-1-hexene, styrene, 4-methyl styrene, 4-isopropyl styrene, 4-tert-butyl styrene, alpha-methyl styrene, 4-tert-butyl-alpha-methyl styrene, 1,3-diisopropenylbenzene, 3-phenyl-1-propene, 1,4-hexadiene, 1,7-octadiene, 3-cyclohexyl-1-butene as well as, 1,3-dienes, butadiene, alkyl alkenoates, e.g., methyl pentenoate, alkenyl alkanoates, alkenyl alkyl ethers, alkenols, e.g., pentenols, alkenals (e.g., pentenals), allyl alcohol, allyl butyrate, hex-1-en-4-ol, oct-1-en-4-ol, vinyl acetate, allyl acetate, 3-butenyl acetate, vinyl propionate, allyl propionate, methyl methacrylate, vinyl ethyl ether, vinyl methyl ether, allyl ethyl ether, n-propyl-7-octenoate, 3-butenenitrile, 5-hexenamide, eugenol, iso-eugenol, safrole, iso-safrole, anethol, 4-allylanisole, indene, limonene, beta-pinene, dicyclopentadiene, cyclooctadiene, camphene, linalool, and the like.

Prochiral and chiral olefins useful in the asymmetric hydroformylation that can be employed to produce enantiomeric aldehyde mixtures include those represented by the formula:

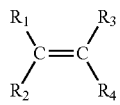

wherein $R_1$, $R_2$, $R_3$ and $R_4$ are the same or different (provided $R_1$ is different from $R_2$ or $R_3$ is different from $R_4$) and are selected from hydrogen; alkyl; substituted alkyl, said substitution being selected from dialkylamino such as benzylamino and dibenzylamino, alkoxy such as methoxy and ethoxy, acyloxy such as acetoxy, halo, nitro, nitrile, thio, carbonyl, carboxamide, carboxaldehyde, carboxyl, carboxylic ester; aryl including phenyl; substituted aryl including phenyl, said substitution being selected from alkyl, amino including alkylamino and dialkylamino such as benzylamino and dibenzylamino, hydroxy, alkoxy such as methoxy and ethoxy, acyloxy such as acetoxy, halo, nitrile, nitro, carboxyl, carboxaldehyde, carboxylic ester, carbonyl, and thio; acyloxy such as acetoxy; alkoxy such as methoxy and ethoxy; amino including alkylamino and dialkylamino such as benzylamino and dibenzylamino; acylamino and diacylamino such as acetylbenzylamino and diacetylamino; nitro; carbonyl; nitrile; carboxyl; carboxamide; carboxaldehyde; carboxylic ester; and alkylmercapto such as methylmercapto. It is understood that the prochiral and chiral olefins of this definition also include molecules of the above general formula where the R groups are connected to form ring compounds, e.g., 3-methyl-1-cyclohexene, and the like.

Illustrative optically active or prochiral olefinic compounds useful in asymmetric hydroformylation include, for example, p-isobutylstyrene, 2-vinyl-6-methoxy-2-naphthylene, 3-ethenylphenyl phenyl ketone, 4-ethenylphenyl-2-thienylketone, 2-ethenyl-5-benzoylthiophene, 3-ethenylphenyl phenyl ether, propenylbenzene, isobutyl-4-propenylbenzene, phenyl vinyl ether and the like. Other olefinic compounds include substituted aryl ethylenes as described, for example, in U.S. Pat. Nos. 4,329,507, 5,360,938 and 5,491,266.

A solvent advantageously is employed in the hydroformylation process. Any suitable solvent that does not unduly interfere with the hydroformylation process can be used. By way of illustration, suitable solvents for rhodium catalyzed hydroformylation processes include those disclosed, for example, in U.S. Pat. Nos. 3,527,809; 4,148,830; 5,312,996; and 5,929,289. Non-limiting examples of suitable solvents include saturated hydrocarbons (alkanes), aromatic hydrocarbons, water, ethers, aldehydes, ketones, nitriles, alcohols, esters, and aldehyde condensation products. Specific examples of solvents include: tetraglyme, pentanes, cyclohexane, heptanes, benzene, xylene, toluene, diethyl ether, tetrahydrofuran, butyraldehyde, and benzonitrile. The organic solvent may also contain dissolved water up to the saturation limit. In general, with regard to the production of achiral (non-optically active) aldehydes, it is preferred to employ aldehyde compounds corresponding to the aldehyde products desired to be produced and/or higher boiling aldehyde liquid condensation by-products as the main organic solvents as is common in the art. Such aldehyde condensation by-products can also be preformed if desired and used accordingly. Illustrative preferred solvents employable in the production of aldehydes include ketones (e.g., acetone and methylethyl ketone), esters (e.g., ethyl acetate, di-2-ethylhexyl phthalate, 2,2,4-trimethyl-1,3-pentanediol monoisobutyrate), hydrocarbons (e.g., toluene), nitrohydrocarbons (e.g., nitrobenzene), ethers (e.g., tetrahydrofuran (THF)) and sulfolane. In rhodium catalyzed hydroformylation processes, it may be preferred to employ, as a primary solvent, aldehyde compounds corresponding to the aldehyde products desired to be produced and/or higher boiling aldehyde liquid condensation by-products, for example, as might be produced in situ during the hydroformylation process, as described for example in U.S. Pat. Nos. 4,148,380 and 4,247,486. Indeed, while one may employ, if desired, any suitable solvent at the start-up of a continuous process, the primary solvent will normally eventually comprise both aldehyde products and higher boiling aldehyde liquid condensation by-products ("heavies"), due to the nature of the continuous process. The amount of solvent is not especially critical and need only be sufficient to provide the reaction medium with the desired amount of transition metal concentration. Typically, the amount of solvent ranges from about 5 percent to about 95 percent by weight, based on the total weight of the reaction fluid. Mixtures of two or more solvents may also be employed.

Illustrative metal-organophosphorous ligand complexes employable in such hydroformylation reactions encompassed by this invention include the metal-organophosphorous ligand complex catalysts as well as methods for their preparation are well known in the art and include those disclosed in the above mentioned patents. In general, such catalysts may be preformed or formed in situ as described in such references and consist essentially of metal in complex combination with an organophosphorous ligand. It is believed that carbon monoxide is also present and complexed with the metal in the active species. The active species may also contain hydrogen directly bonded to the metal.

The catalyst useful in the hydroformylation process includes a metal-organophosphorous ligand complex catalyst which can be optically active or non-optically active. The permissible metals that make up the metal-organophosphorous ligand complexes include Group 8, 9 and 10 metals selected from rhodium (Rh), cobalt (Co), iridium (Ir), ruthenium (Ru), iron (Fe), nickel (Ni), palladium (Pd), platinum (Pt), osmium (Os) and mixtures thereof, with the preferred metals being rhodium, cobalt, iridium and ruthenium, more preferably rhodium, cobalt and ruthenium, especially rhodium. Mixtures of metals from Groups 8, 9 and 10 may also be employed.

The number of available coordination sites on such metals is well known in the art. Thus the catalytic species may comprise a complex catalyst mixture, in their monomeric, dimeric or higher nuclearity forms, which are preferably characterized by at least one organophosphorous ligand-containing molecule complexed per one molecule of metal, e.g., rhodium. For instance, it is considered that the catalytic species of the preferred catalyst employed in a hydroformylation reaction may be complexed with carbon monoxide and hydrogen in addition to the organophosphorous ligands in view of the carbon monoxide and hydrogen gas employed by the hydroformylation reaction.

The permissible organophosphorous ligands which make up the metal-organophosphorous ligand complexes and free organophosphorous ligand include triarylphosphines and hydrolyzable organophosphorous ligands such as mono-, di-, tri- and higher polyorganophosphites. Mixtures of such ligands may be employed if desired in the metal-organophosphorous ligand complex catalyst and/or free ligand and such mixtures may be the same or different. This invention is not intended to be limited in any manner by the permissible organophosphorous ligands or mixtures thereof. It is to be noted that the successful practice of this invention does not depend and is not predicated on the exact structure of the metal-organophosphorous ligand complex species, which may be present in their mononuclear, dinuclear and/or higher nuclearity forms. Indeed, the exact structure is not known. While not intending to be bound to any theory or mechanistic discourse, it appears that the catalytic species may in its simplest form consist essentially of the metal in complex combination with the organophosphorous ligand and carbon monoxide and/or hydrogen.

The term "complex" as used herein and in the claims means a coordination compound formed by the union of one or more electronically rich molecules or atoms capable of independent existence with one or more electronically poor molecules or atoms, each of which is also capable of independent existence. For example, the organophosphorous ligands employable herein may possess one or more phosphorus donor atoms, each having one available or unshared pair of electrons that are each capable of forming a coordinate bond independently or possibly in concert (e.g., via chelation) with the metal. Among the organophosphorous ligands that may serve as the ligand of the metal-organophosphorous ligand complex catalyst are fluorophosphites, phosphinites, phosphino-phosphoramidites, monoorganophosphite, diorganophosphite, triorganophosphite, organopolyphosphite, phosphoramidites, organomonophosphoramidite and organopolyphosphoramidite compounds. Such organophosphorous ligands and/or methods for their preparation are well known in the art. Mixtures of the above ligands can also be used. Carbon monoxide (which is also properly classified as a ligand) can also be present and coordinated to the metal. The ultimate composition of the complex catalyst may also contain an additional ligand, e.g., hydrogen or an anion satisfying the coordination sites or nuclear charge of the metal. Illustrative additional ligands include, for example, halogen (Cl, Br, I), alkyl, aryl, substituted aryl, acyl, $CF_3$, $C_2F_5$, CN, $(R)_2PO$ and $RP(O)(OH)O$ (wherein each R is the same or different and is a substituted or unsubstituted hydrocarbon radical, e.g., the alkyl or aryl), acetate, acetylacetonate, $SO_4$, $PF_4$, $PF_6$, $NO_2$, $NO_3$, $CH_3$, $CH_2=CHCH_2$, $CH_3CH=CHCH_2$, $C_6H_5CN$, $CH_3CN$, $NH_3$, pyridine, $(C_2H_5)_3N$, mono-olefins, diolefins and triolefins, tetrahydrofuran, and the like. It is to be understood that the complex species are preferably free of any additional organic ligand or anion that might poison the catalyst or have an undue adverse effect on catalyst performance. It is preferred in the metal-organophosphorous ligand complex catalyzed hydroformylation reactions that the active catalysts be free of halogen and sulfur directly bonded to the metal, although such may not be absolutely necessary.

The organophosphorous compounds that may serve as the ligand of the metal-organophosphorous ligand complex catalyst and/or free ligand may be of the achiral (optically inactive) or chiral (optically active) type and are well known in the art. Achiral organophosphorous ligands are preferred.

Representative monoorganophosphites may include those having the formula:

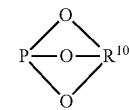

<<I>> wherein $R^{10}$ represents a substituted or unsubstituted trivalent hydrocarbon radical containing from 4 to 40 carbon atoms or greater, such as trivalent acyclic and trivalent cyclic radicals, e.g., trivalent alkylene radicals such as those derived from 1,2,2-trimethylolpropane and the like, or trivalent cycloalkylene radicals such as those derived from 1,3,5-trihydroxycyclohexane, and the like. Such monoorganophosphites may be found described in greater detail, for example, in U.S. Pat. No. 4,567,306.

Representative diorganophosphites may include those having the formula:

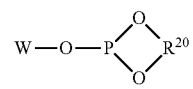

<<II>> wherein $R^{20}$ represents a substituted or unsubstituted divalent hydrocarbon radical containing from 4 to 40 carbon atoms or greater and W represents a substituted or unsubstituted monovalent hydrocarbon radical containing from 1 to 18 carbon atoms or greater.

Representative substituted and unsubstituted monovalent hydrocarbon radicals represented by W in the above Formula (II) include alkyl and aryl radicals, while representative substituted and unsubstituted divalent hydrocarbon radicals represented by $R^{20}$ include divalent acyclic radicals and divalent aromatic radicals. Illustrative divalent acyclic radicals include, for example, alkylene, alkylene-oxy-alkylene, alkylene-S-alkylene, cycloalkylene radicals, and, alkylene-$NR^{24}$-alkylene wherein $R^{24}$ is hydrogen or a substituted or unsubstituted monovalent hydrocarbon radical, e.g., an alkyl radical having 1 to 4 carbon atoms. The more preferred divalent acyclic radicals are the divalent alkylene radicals such as disclosed more fully, for example, in U.S. Pat. Nos. 3,415,906 and 4,567,302 and the like. Illustrative divalent aromatic radicals include, for example, arylene, bisarylene, arylene-alkylene, arylene-alkylene-arylene, arylene-oxy-arylene, arylene-NR$^{24}$-arylene wherein R$^{24}$ is as defined above, arylene-S-arylene, and arylene-S-alkylene, and the like. More preferably R$^{20}$ is a divalent aromatic radical such as disclosed more fully, for example, in U.S. Pat. Nos. 4,599,206, 4,717,775, 4,835,299, and the like.

Representative of a more preferred class of diorganophosphites are those of the formula:

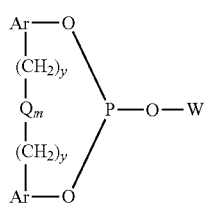

<<III>> wherein W is as defined above, each Ar is the same or different and represents a substituted or unsubstituted aryl radical, each y is the same or different and is a value of 0 or 1, Q represents a divalent bridging group selected from —C(R$^{33}$)$_2$—, —O—, —S—, —NR$^{24}$—, Si(R$^{35}$)$_2$ and —CO—, wherein each R$^{33}$ is the same or different and represents hydrogen, an alkyl radical having from 1 to 12 carbon atoms, phenyl, tolyl, and anisyl, R$^{24}$ is as defined above, each R$^{35}$ is the same or different and represents hydrogen or a methyl radical, and m has a value of 0 or 1. Such diorganophosphites are described in greater detail, for example, in U.S. Pat. Nos. 4,599,206, 4,717,775, and 4,835,299.

Representative triorganophosphites may include those having the formula:

<<IV>> wherein each R$^{46}$ is the same or different and is a substituted or unsubstituted monovalent hydrocarbon radical e.g., an alkyl, cycloalkyl, aryl, alkaryl and aralkyl radicals that may contain from 1 to 24 carbon atoms. Such triorganophosphites are described in greater detail, for example, in U.S. Pat. Nos. 3,527,809 and 5,277,532.

Representative organopolyphosphites contain two or more tertiary (trivalent) phosphorus atoms and may include those having the formula:

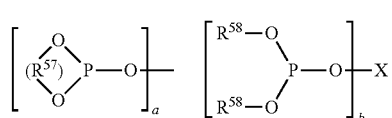

<<V>> wherein X represents a substituted or unsubstituted n-valent organic bridging radical containing from 2 to 40 carbon atoms, each R$^{57}$ is the same or different and represents a divalent organic radical containing from 4 to 40 carbon atoms, each R$^{58}$ is the same or different and represents a substituted or unsubstituted monovalent hydrocarbon radical containing from 1 to 24 carbon atoms, a and b can be the same or different and each have a value of 0 to 6, with the proviso that the sum of a+b is 2 to 6 and n equals a+b. It is to be understood that when a has a value of 2 or more, each R$^{57}$ radical may be the same or different. Each R$^{58}$ radical may also be the same or different in any given compound.

Representative n-valent (preferably divalent) organic bridging radicals represented by X and representative divalent organic radicals represented by R$^{57}$ above, include both acyclic radicals and aromatic radicals, such as alkylene, alkylene-Q$_m$-alkylene, cycloalkylene, arylene, bisarylene, arylene-alkylene, and arylene-(CH$_2$)$_y$-Q$_m$-(CH$_2$)$_y$-arylene radicals, and the like, wherein each Q, y and m are as defined above in Formula (III). The more preferred acyclic radicals represented by X and R$^{57}$ above are divalent alkylene radicals, while the more preferred aromatic radicals represented by X and R$^{57}$ above are divalent arylene and bisarylene radicals, such as disclosed more fully, for example, in U.S. Pat. Nos. 4,769,498; 4,774,361: 4,885,401; 5,179,055; 5,113,022; 5,202,297; 5,235,113; 5,264,616 and 5,364,950, and 5,527,950. Representative preferred monovalent hydrocarbon radicals represented by each R$^{58}$ radical above include alkyl and aromatic radicals.

Illustrative preferred organopolyphosphites may include bisphosphites such as those of Formulas (VI) to (VIII) below:

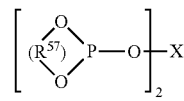

<<VI>>

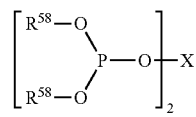

<<VII>>

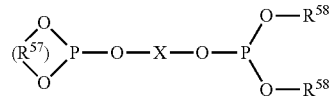

<<VIII>> wherein each R$^{57}$, R$^{58}$ and X of Formulas (VI) to (VIII) are the same as defined above for Formula (V). Preferably each R$^{57}$ and X represents a divalent hydrocarbon radical selected from alkylene, arylene, arylene-alkylene-arylene, and bisarylene, while each R$^{58}$ radical represents a monovalent hydrocarbon radical selected from alkyl and aryl radicals. Organophosphite ligands of such Formulas (V) to (VIII) may be found disclosed, for example, in U.S. Pat. Nos. 4,668,651; 4,748,261; 4,769,498; 4,774,361; 4,885,401; 5,113,022; 5,179,055; 5,202,297; 5,235,113; 5,254,741; 5,264,616; 5,312,996; 5,364,950; and 5,391,801.

R$^{10}$, R$^{20}$, R$^{46}$, R$^{57}$, R$^{58}$, Ar, Q, X, m, and y in Formulas (VI) to (VIII) are as defined above. Most preferably X represents a divalent aryl-(CH$_2$)$_y$-(Q)$_m$-(CH$_2$)y-aryl radical wherein each y individually has a value of 0 or 1; m has a value of 0 or 1 and Q is —O—, —S— or —C(R$^{35}$)$_2$— where each R$^{35}$ is the same or different and represents hydrogen or a methyl radical. More preferably each alkyl radical of the above defined R$^8$ groups may contain from 1 to 24 carbon atoms and each aryl radical of the above-defined Ar, X, $R^{57}$ and $R^{58}$ groups of the above Formulas (VI) to (VII) may contain from 6 to 18 carbon atoms and said radicals may be the same or different, while the preferred alkylene radicals of X may contain from 2 to 18 carbon atoms and the preferred alkylene radicals of $R^{57}$ may contain from 5 to 18 carbon atoms. In addition, preferably the divalent Ar radicals and divalent aryl radicals of X of the above formulas are phenylene radicals in which the bridging group represented by —$(CH_2)_y$-$(Q)_m$-$(CH_2)_y$— is bonded to said phenylene radicals in positions that are ortho to the oxygen atoms of the formulas that connect the phenylene radicals to their phosphorus atom of the formulae. It is also preferred that any substituent radical when present on such phenylene radicals be bonded in the para and/or ortho position of the phenylene radicals in relation to the oxygen atom that bonds the given substituted phenylene radical to its phosphorus atom.

Any of the $R^{10}$, $R^{20}$, $R^{57}$, $R^{58}$, W, X, Q and Ar radicals of such organophosphites of Formulas (I) to (VIII) above may be substituted if desired, with any suitable substituent containing from 1 to 30 carbon atoms that does not unduly adversely affect the desired result of the process of this invention. Substituents that may be on said radicals in addition to corresponding hydrocarbon radicals such as alkyl, aryl, aralkyl, alkaryl and cyclohexyl substituents, may include for example silyl radicals such as —$Si(R^{15})_3$; amino radicals such as —$N(R^{15})_2$; phosphine radicals such as -aryl-$P(R^{15})_2$; acyl radicals such as —$C(O)R^{15}$ acyloxy radicals such as —$OC(O)R^{15}$; amido radicals such as —$CON(R^{15})_2$ and —$N(R^{15})COR^{15}$; sulfonyl radicals such as —$SO_2R^{15}$, alkoxy radicals such as —$OR^{15}$; sulfinyl radicals such as —$SOR^{15}$, phosphonyl radicals such as —$P(O)(R^{15})_2$, as well as halo, nitro, cyano, trifluoromethyl, hydroxy radicals, and the like, wherein each $R^{15}$ radical individually represents the same or different monovalent hydrocarbon radical having from 1 to 18 carbon atoms (e.g., alkyl, aryl, aralkyl, alkaryl and cyclohexyl radicals), with the proviso that in amino substituents such as —$N(R^{15})_2$ each $R^{15}$ taken together can also represent a divalent bridging group that forms a heterocyclic radical with the nitrogen atom, and in amido substituents such as —$C(O)N(R^{15})_2$ and —$N(R^{15})COR^{15}$ each $R^{15}$ bonded to N can also be hydrogen. It is to be understood that any of the substituted or unsubstituted hydrocarbon radicals groups that make up a particular given organophosphite may be the same or different.

As a further option, any organomonophosphoramidite or organopolyphosphoramidite ligand can be used as the, or in combination with any other, organophosphorous ligand. Organophosphoramidite ligands are known, and they are used in the same manner as organophosphite ligands. Representative organophosphoramidite ligands are of formulae IX-XI.

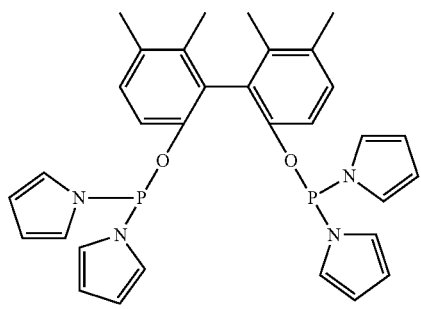

(IX)

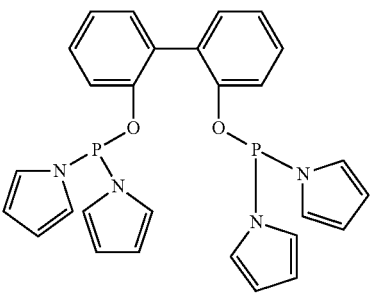

(X)

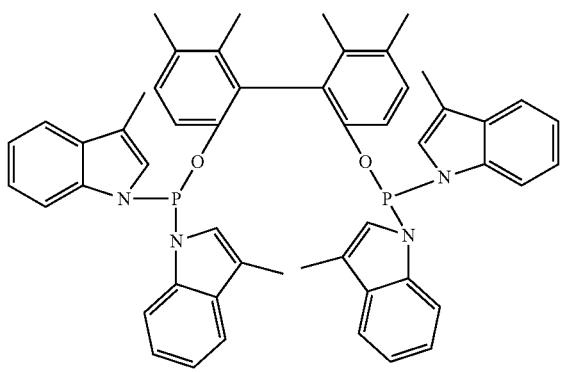

(XI)

Organophosphoramidites are further described in, for example, U.S. Pat. No. 7,615,645.

The triarylphosphine employable in the process of this disclosure comprises any organic compound comprising at least one phosphorus atom covalently bonded to three aryl or arylalkyl radicals, or combinations thereof. A mixture of triarylphosphine ligands may also be employed. Representative organomonophosphines include those having the formula:

(XII)

wherein each $R^{29}$, $R^{30}$ and $R^{31}$ may be the same or different and represent a substituted or unsubstituted aryl radical containing from 4 to 40 carbon atoms or greater. Such triarylphosphines may be found described in greater detail, for example, in U.S. Pat. No. 3,527,809, the disclosure of which is incorporated herein by reference. Illustrative triarylphosphine ligands are triphenylphosphine, trinaphthylphine, tritolylphosphine, tri(p-biphenyl)phosphine, tri(p-methoxyphenyl) phosphine, tri(m-chlorophenyl)-phosphine, p-N,N-dimethylaminophenyl bis-phenyl phosphine, and the like. Triphenyl phosphine, i.e., the compound of Formula I wherein each $R^{29}$, $R^{30}$ and $R^{31}$ is phenyl, is an example of a preferred organomonophosphine ligand. The hydroformylation reaction is preferentially effected in a liquid body containing excess, free triarylphosphine.

As noted above, the metal-organophosphorous ligand complex catalysts may be formed by methods known in the art. The metal-organophosphorous ligand complex catalysts may be in homogeneous or heterogeneous form. For instance, preformed rhodium hydrido-carbonyl-organophosphorous ligand catalysts may be prepared and introduced into the reaction mixture of a hydroformylation process. More preferably, the rhodium-organophosphorous ligand complex catalysts can be derived from a rhodium catalyst precursor which may be introduced into the reaction medium for in situ formation of the active catalyst. For example, rhodium catalyst precursors such as rhodium dicarbonyl acetylacetonate, $Rh_2O_3$, $Rh_4(CO)_{12}$, $Rh_6(CO)_{16}$, $Rh(NO_3)_3$, and the like may be introduced into the reaction mixture along with the organophosphorous ligand for the in situ formation of the active catalyst. In a preferred embodiment of this invention, rhodium dicarbonyl acetylacetonate is employed as a rhodium precursor and reacted in the presence of a solvent with the organophosphorous ligand to form a catalytic rhodium-organophosphorous ligand complex precursor which is introduced into the reactor along with excess (free) organophosphorous ligand for the in situ formation of the active catalyst. In any event, it is sufficient for the purposes of this invention that carbon monoxide, hydrogen and organophosphorous ligand compound are all ligands that are capable of being complexed with the metal and that an active metal-organophosphorous ligand catalyst is present in the reaction mixture under the conditions used in the hydroformylation reaction. Carbonyl and organophosphorous ligands, if not already complexed with the initial rhodium, may be complexed to the rhodium either prior to or in situ during the hydroformylation process.

By way of illustration, the preferred catalyst precursor composition consists essentially of a solubilized rhodium carbonyl organophosphorous ligand complex precursor, a solvent and, optionally, free organophosphorous ligand. The preferred catalyst precursor composition can be prepared by forming a solution of rhodium dicarbonyl acetylacetonate, an organic solvent and a organophosphorous ligand. The organophosphorous ligand readily replaces one of the carbonyl ligands of the rhodium acetylacetonate complex precursor at room temperature as witnessed by the evolution of carbon monoxide gas. This substitution reaction may be facilitated by heating the solution if desired. Any suitable organic solvent in which both the rhodium dicarbonyl acetylacetonate complex precursor and rhodium organophosphorous ligand complex precursor are soluble can be employed. The amounts of rhodium complex catalyst precursor, organic solvent and organophosphorous ligand, as well as their preferred embodiments present in such catalyst precursor compositions may obviously correspond to those amounts employable in the hydroformylation process of this invention. Experience has shown that the acetylacetonate ligand of the precursor catalyst is replaced after the hydroformylation process has begun with a different ligand, e.g., hydrogen, carbon monoxide or organophosphorous ligand, to form the active complex catalyst as explained above. The acetylacetone which is freed from the precursor catalyst under hydroformylation conditions is removed from the reaction medium with the product aldehyde and thus is in no way detrimental to the hydroformylation process. The use of such preferred rhodium complex catalytic precursor compositions provides a simple economical and efficient method for handling the rhodium precursor and hydroformylation start-up.

Accordingly, the metal-organophosphorous ligand complex catalyst used in the process of this invention consists essentially of the metal complexed with carbon monoxide and a organophosphorous ligand, said ligand being bonded (complexed) to the metal in a chelated and/or non-chelated fashion. Moreover, the terminology "consists essentially of", as used herein, does not exclude, but rather includes, hydrogen complexed with the metal, in addition to carbon monoxide and the organophosphorous ligand. Further, such terminology does not exclude the possibility of other organic ligands and/or anions that might also be complexed with the metal. Materials in amounts which unduly adversely poison or unduly deactivate the catalyst are not desirable and so the catalyst most desirably is free of contaminants such as metal-bound halogen (e.g., chlorine, and the like) although such may not be absolutely necessary. The hydrogen and/or carbonyl ligands of an active metal-organophosphorous ligand complex catalyst may be present as a result of being ligands bound to a precursor catalyst and/or as a result of in situ formation, e.g., due to the hydrogen and carbon monoxide gases employed in hydroformylation process.

As noted, the hydroformylation process of this invention involves the use of a metal-organophosphorous ligand complex catalyst as described herein. Mixtures of such catalysts can also be employed if desired. The amount of metal-organophosphorous ligand complex catalyst present in the reaction fluid of a given hydroformylation process encompassed by this invention need only be that minimum amount necessary to provide the given metal concentration desired to be employed and which will furnish the basis for at least the catalytic amount of metal necessary to catalyze the particular hydroformylation process involved such as disclosed, for example, in the above-mentioned patents. In general, catalytic metal, e.g., rhodium, concentrations in the range of from 10 ppmw to 1000 ppmw, calculated as free metal in the reaction medium, should be sufficient for most processes, while it is generally preferred to employ from 10 to 500 ppmw of metal, and more preferably from 25 to 350 ppmw of metal.

In addition to the metal-organophosphorous ligand complex catalyst, free organophosphorous ligand (i.e., ligand that is not complexed with the metal) may also be present in the reaction medium. The free organophosphorous ligand may correspond to any of the above-defined organophosphorous ligands discussed above as employable herein. It is preferred that the free organophosphorous ligand be the same as the organophosphorous ligand of the metal-organophosphorous ligand complex catalyst employed. However, such ligands need not be the same in any given process. The hydroformylation process may involve from 0.1 moles or less to 100 moles or higher of free organophosphorous ligand per mole of metal in the reaction medium. Preferably, the hydroformylation process is carried out in the presence of from 1 to 50 moles of organophosphorous ligand per mole of metal present in the reaction medium. More preferably, for organopolyphosphites, from 1.1 to 4 moles of organopolyphosphite ligand are employed per mole of metal. Said amounts of organophosphorous ligand are the sum of both the amount of organophosphorous ligand that is bound (complexed) to the metal present and the amount of free (non-complexed) organophosphorous ligand present. Since it is more preferred to produce non-optically active aldehydes by hydroformylating achiral olefins, the more preferred organophosphorous ligands are achiral type organophosphorous ligands, especially those encompassed by Formula (V) above, and more preferably those of Formulas (VI), (VII) and (VIII) above. If desired, make-up or additional organophosphorous ligand can be supplied to the reaction medium of the hydroformylation process at any time and in any suitable manner, e.g., to maintain a predetermined level of free ligand in the reaction medium.

As indicated above, the hydroformylation catalyst may be in heterogeneous form during the reaction and/or during the product separation. Such catalysts are particularly advantageous in the hydroformylation of olefins to produce high boiling or thermally sensitive aldehydes, so that the catalyst may be separated from the products by filtration or decantation at low temperatures. For example, the rhodium catalyst may be attached to a support so that the catalyst retains its solid form during both the hydroformylation and separation stages, or is soluble in a liquid reaction medium at high temperatures and then is precipitated on cooling.

The use of an aqueous extraction system, preferably employing a buffer solution, to prevent and/or lessen hydrolytic degradation of an organophosphorous ligand and deactivation of a metal-organophosphorous ligand complex is well-known and is disclosed, e.g., in U.S. Pat. Nos. 5,741,942 and 5,741,944. Such buffer systems and/or methods for their preparation are well known in the art. Mixtures of buffers may be employed.

Illustrative metal-organophosphorous ligand complex catalyzed hydroformylation processes that may experience hydrolytic degradation include those processes as described, for example, in U.S. Pat. Nos. 4,148,830; 4,593,127; 4,769,498; 4,717,775; 4,774,361; 4,885,401; 5,264,616; 5,288,918; 5,360,938; 5,364,950; 5,491,266 and 7,196,230. P—Z containing species that will likely undergo hydrolytic degradation include organophosphonites, phosphoramidites, fluorophosphonites, and the like such as described WO 2008/071508, WO 2005/042458, and U.S. Pat. Nos. 5,710,344, 6,265,620, 6,440,891, 7,009,068, 7,145,042, 7,586,010, 7,674,937, and 7,872,156. These species will generate a variety of acidic and/or polar degradation products that can be extracted by use of the extractor technology taught in U.S. Pat. Nos. 5,744,649 and 5,741,944. Accordingly, the hydroformylation processing techniques that are advantageously employed with the invention disclosed herein may correspond to any known processing techniques. Preferred hydroformylation processes are those involving catalyst liquid recycle.

Extraction contacting conditions may vary greatly and any suitable combination of such conditions may be employed herein. For instance, a decrease in one of such conditions may be compensated for by an increase in one or more of the other conditions, while the corollary is also true. In general, liquid temperatures ranging from 10° C. to 120° C., preferably from 20° C. to 80° C., and more preferably from 25° C. to 60° C., should be suitable for most instances, although lower or higher temperatures may be employed if desired. Advantageously, the treatment is carried out at pressures ranging from ambient to reaction pressure, and the contact time may vary from a matter of seconds or minutes to a few hours or more.

Success in removing phosphorus acidic compounds from the reaction fluid may be determined by measuring the rate of degradation (consumption) of the organophosphorous ligand present in the hydroformylation reaction medium. The consumption rate can vary over a wide range, e.g., from <0.6 up to 5 grams per liter per day, and will be governed by the best compromise between cost of ligand and treatment frequency to keep hydrolysis below autocatalytic levels. Preferably, the aqueous buffer solution treatment is carried out in such a manner that the consumption of the desired organophosphorous ligand present in the hydroformylation reaction medium is maintained at an acceptable rate, e.g., <0.5 grams of ligand per liter per day, and more preferably <0.1 grams of ligand per liter per day, and most preferably <0.06 grams of ligand per liter per day. As the neutralization and extraction of phosphorus acidic compounds into the aqueous buffer solution proceeds, the pH of the buffer solution will slowly decrease.

The removal of at least some amount of phosphorus acidic compounds, for example, $H_3PO_3$, $H_3PO_4$, aldehyde acids such as hydroxy alkyl phosphonic acids, such as hydroxyl butyl phosphonic acid and hydroxyl pentyl phosphonic acid, and the like, from the hydroformylation system allows one to control the acidity of the hydroformylation reaction medium, thereby stabilizing the useful organophosphorous ligand by preventing or lessening its hydrolytic decomposition.

Optionally, an organic nitrogen compound may be added to the hydroformylation reaction fluid to scavenge the acidic hydrolysis by-products formed upon hydrolysis of the organophosphorous ligand, as taught, for example, in U.S. Pat. No. 4,567,306. Such organic nitrogen compounds may be used to react with and to neutralize the acidic compounds by forming conversion product salts therewith, thereby preventing the catalytic metal from complexing with the acidic hydrolysis by-products and thus helping to protect the activity of the catalyst while it is present in the reaction zone under reaction conditions.

Preferred organic nitrogen compounds useful for scavenging the phosphorus acidic compounds are heterocyclic compounds selected from the group consisting of diazoles, triazoles, diazines and triazines, and the like, such as those disclosed in U.S. Pat. No. 5,731,472.

Benzimidazole and benztriazole are preferred. The amount of organic nitrogen compound that may be present in the reaction fluid is typically sufficient to provide a concentration of at least 0.0001 moles of free organic nitrogen compound per liter of reaction fluid. In general, the ratio of organic nitrogen compound to total organophosphorous ligand (whether bound or present as free organophosphorous ligand) is at least 0.1:1 and even more preferably at least 0.5:1. Organic nitrogen compound: organophosphorous ligand molar ratios of from 1:1 to 5:1 should be sufficient for most purposes.

The aqueous buffer solution treatment will not only remove free phosphoric acidic compounds from the metal-organophosphorous ligand complex catalyst containing reaction fluids, but it also removes the phosphorus acidic material of the conversion product salt formed by the use of the organic nitrogen compound scavenger when employed, i.e., the phosphorus acid of said conversion product salt remains behind in the aqueous buffer solution, while the treated reaction fluid, along with the reactivated (free) organic nitrogen compound is returned to the reaction zone.

When using hydrolyzable ligands, it is preferred to employ means to remove ligand degradation products from the process to avoid acid-catalyzed autocatalytic ligand degradation. The use of extractors, amine additives, epoxides and other means are known for control and/or removal of these degradation products. See, e.g., (U.S. Pat. Nos. 5,741,942, 5,741,944, JP 3864668, U.S. Pat. Nos. 5,648,554, 5,731,473, 5,744,649, 5,789,625, 6,846,960, and 6,995,292. These degradation product control means are advantageously implemented on the catalyst recycle stream, and can be located before or after the recycle stream is split following the vaporizer.

The process of the invention employs a primary reactor followed by a product-catalyst separation zone. The separation zone produces a crude product stream and a catalyst recycle stream. The crude product stream comprises the desired aldehyde product as well as unreacted raw materials, such as olefin and syngas. An unrefined product stream is separated from the unreacted raw materials following the product-catalyst separation zone using techniques well known to those skilled in the art. The unreacted raw materials are then supplied to a separate, secondary reactor, and the liquid output from the secondary reactor is fed to the same product-catalyst separation zone. The catalyst recycle stream from the product-catalyst separation zone is split, with a portion being recycled to the primary reactor and a portion being recycled to the secondary reactor. In one embodiment, a portion of the liquid effluent from the secondary reactor is sent to the primary reactor upstream of the product-catalyst separation zone.

The process of the invention employs a secondary reactor, which may be the same type or different than the primary reactor. The feed for this reactor primarily comprises unreacted reactants from the product-catalyst separation zone, but may incorporate streams from other sources.

The hydroformylation process may be carried out using one or more suitable reactor types such as, for example, a tubular reactor, venturi reactor, a bubble column reactor, or a continuous stirred tank reactor. A reaction zone may be fitted with one or more internal and/or external heat exchanger(s) in order to control temperature fluctuations, and to prevent any possible "runaway" reaction temperatures.

Each reactor vessel may comprise a single reaction zone or multiple reaction zones, such as, for example, described in U.S. Pat. No. 5,728,893. In one embodiment of the invention, two reaction zones are present in a single reactor vessel. The term "first reaction zone" refers to the first reaction zone in the primary reactor. Multistaged reactors can be designed with internal, physical barriers that create more than one reaction zone or theoretical reactive stage per vessel. In effect, a number of reactor zones are contained inside a single continuous stirred tank reactor vessel. Putting multiple reaction zones in a single vessel is a cost effective way of using reactor vessel volume, and significantly reduces the number of vessels that otherwise would be required to achieve the same results. Fewer vessels reduces the overall capital required and maintenance concerns associated with having separate vessels and agitators. Within a reactor, reaction zones can be arranged in series or in parallel.

The choice of suitable materials of construction for process equipment can be readily made by those skilled in the art. The materials employed should be substantially inert to the starting materials and the reaction mixture, and the process equipment should be able to withstand the reaction temperatures and pressures. For example, the hydroformylation processes may be conducted in either glass lined, stainless steel or similar type reaction equipment.

Means to introduce and/or adjust the quantity of starting materials or ingredients introduced batchwise, semi-continuously or continuously into the reaction zone during the course of the reaction can be conveniently utilized in the process, and such means are useful to maintain the desired molar ratio of the starting materials. The reaction steps may be effected by the incremental addition of one of the starting materials to the other.

In one embodiment of the invention, the catalytic metal concentration in the primary reactor is determined indirectly according to methods well known to those skilled in the art. For example, the relative concentration of aldehyde heavies, ligands, ligand decomposition products (oxides, etc.), or other markers, which correlate to the rhodium, can be analyzed by gas chromatography, HPLC, UV-Vis or IR spectroscopy and other well known techniques.

If the catalytic metal concentration is too high or too low, the fraction of the total catalyst recycle mass from the vaporizer can be lowered or raised, respectively, in order to effect the desired change to the catalytic metal concentration in the primary reactor.

The concentration of catalytic metal in the primary reactor can be correlated to the mass ratio of (a) fresh olefin fed to the primary reactor to (b) the amount of feed sent to the secondary reactor. Based on this ratio, the metal concentration in the primary reactor is controlled according to the mass ratio of catalyst recycle streams fed to the primary reactor. The relevant flow rates can be measured using mass flow meters.

Ethylene and propylene hydroformylation reaction kinetics are more responsive to changes in the kinetic variables than the kinetics for higher olefins. Thus, one preferred control scheme will control the catalytic metal concentration of the primary reactor and will allow the catalytic metal concentration in the secondary reactor to vary or "float." The concentration of catalytic metal in a reactor can be controlled by monitoring the olefin partial pressure in the reactor. For a given temperature and CO partial pressure, the olefin partial pressure generally is a function of catalytic metal content; thus, if olefin partial pressure is out of the desired range, then the catalyst recycle flow can be adjusted to keep the olefin partial pressure within the desired range based on known kinetics for the catalyst. This "inferential control" can employ commercially available monitoring systems.

The process may be conducted in any batch, continuous or semi-continuous fashion and may involve any catalyst liquid and/or gas recycle operation desired. It is generally preferred to carry out the hydroformylation process in a continuous manner Continuous hydroformylation processes are well known in the art.

The reaction conditions of the hydroformylation process within each reactor may include any suitable type hydroformylation conditions heretofore employed for producing optically active and/or non-optically active aldehydes. For instance, the total gas pressure of hydrogen, carbon monoxide and olefin starting compound of the hydroformylation process may range from 100 to 69,000 kPa. In general, however, it is preferred that the process be operated at a total gas pressure of hydrogen, carbon monoxide and olefin starting compound of less than 14,000 kPa and more preferably less than 3,400 kPa. The minimum total pressure is limited predominantly by the amount of reactants necessary to obtain a desired rate of reaction. More specifically the carbon monoxide partial pressure of the hydroformylation process is preferably from 1 to 6,900 kPa, and more preferably from 21 to 5,500 kPa, while the hydrogen partial pressure is preferably from 34 to 3,400 kPa and more preferably from 69 to 2,100 kPa. In general, $H_2$: CO molar ratio of gaseous hydrogen to carbon monoxide may range from 1:10 to 100:1 or higher, the more preferred hydrogen to carbon monoxide molar ratio being from 1:10 to 10:1.

In general, the hydroformylation process may be conducted at any operable reaction temperature. Advantageously, the hydroformylation process is conducted at a reaction temperature of from −25° C. to 200° C. In general, hydroformylation reaction temperatures of 50° C. to 120° C. are preferred for all types of olefinic starting materials. As is known to those skilled in the art, the hydroformylation reaction conditions employed are governed by the type of aldehyde product desired.

It is well known that the product N:I ratio of linear and branched aldehyde isomers is dependent on a number of factors including ligand identity and concentration (usually defined as the ligand-to-rhodium ratio), temperature, and CO and H$_2$ partial pressures. Known methods for controlling the N:I ratio may be employed in the process of the invention. For example, each reactor can have different Rh concentrations, CO and H$_2$ partial pressures, and temperatures.

In one embodiment, the temperature and CO and H$_2$ partial pressures in the primary and secondary reactors can be the same or different to optimize conversion and N:I ratio within each reactor. Additionally, the temperatures and partial pressures in different reactors may be optimized separately. Within each reactor, the CO and H$_2$ partial pressures can be optimized and changed independently to adjust for changes in rhodium concentrations and residence times which may result in changes in the catalyst recycle rate and rhodium concentration. This allows for enhanced reactor stability and product N:I ratio control.

In one embodiment, one reactor may be run under "isomerizing conditions" as taught in U.S. Pat. No. 7,615,645.

In yet another embodiment, as the feed rates to the primary reactor change, the residence time in each reactor will change and thus the reactor temperature(s) within the primary and secondary reactor can be further optimized without impacting the other reactor. For example, if the feed supply to the primary reactor is reduced, the residence time within the primary reactor will increase. Since the conversion is already close to 100%, this longer residence time is not contributing to production but only contributes to higher ligand degradation and heavies formation. Therefore, the reactor temperatures can be reduced to reduce these losses without losing significant olefin conversion.

It is well known that the reaction rate is a function of temperature and catalyst concentration, among other factors. The rate of conversion is controlled primarily by controlling the temperature of the reaction mass and the concentration of the catalyst in each reactor. In one embodiment, the flow rate of at least one of the catalyst recycle streams is controlled in order to control the concentration of catalyst in the primary reactor. In one embodiment of the invention, the control is effected by setting the desired catalytic metal concentration for the primary reactor. In one embodiment of the invention, the catalytic metal concentration value in the primary reactor is determined directly by analytical methods, which can be performed online or offline. Examples of direct analytical methods include inductively coupled plasma mass spectroscopy, atomic absorption spectroscopy, high pressure liquid chromatography (HPLC) and X-ray fluorescence.

At a given temperature, all else being equal, the hydroformylation reaction rate is directly proportional to the catalytic metal concentration. The catalytic metal concentration in each reactor is related to the mass flow rate and catalytic metal concentration of each recycle stream. Thus, the hydroformylation reaction rate is a function of the recycle mass flow rate and the concentration of catalyst catalytic metal in the recycle stream.

Without being bound by theory, it is thought that by concentrating the vaporizer vent stream, having removed the aldehyde product, the resulting olefin-containing stream is more concentrated than in the last reaction zone of the primary reactor. Delivering this enriched olefin stream to fresh recycled catalyst stream results in higher olefin and/or catalyst concentration in the secondary reactor compared to the last reaction zone of the primary reactor. This gives a much higher relative reaction rate for the residual raw materials. Since this stream is much smaller than the original feed, a much smaller reactor is needed, saving capital expense. In one embodiment of the invention, the volume of the secondary reactor is no more than 80% of the volume of the primary reactor. Advantageously, the volume of the secondary reactor is no more than 70% of the volume of the primary reactor, preferably no more than 50%, more preferably no more than 35%, and even more preferably no more than 25%. This smaller reactor can be at elevated temperature, CO partial pressure, and/or rhodium concentration, compared to conditions in the primary reactor, to achieve very high conversion but since only a small portion of the total reaction fluid is under these conditions, the total amount of ligand degradation and heavies formation is much lower than if an additional, full sized reactor was added in the primary reaction zone. By combining the output of the secondary reactor with the primary reactor by using only one vaporizer, additional capital savings are realized. Additional capital savings result from the smaller size of the secondary reactor.

There is a relationship between the size of the secondary reactor, the mass flow rate of catalyst recycle stream, and the mass flow rate of the vent stream being fed to the secondary reactor. This relationship determines the average residence time in the secondary reactor. In various embodiments of the invention, the residence time in the secondary reactor is at least 20%, at least 50%, or at least 75% longer than the residence time in the primary reactor. Since the amount of ligand decomposition and aldehyde heavies formation are related to the volume of the reaction fluid, a smaller total reaction fluid mass will result in lower amounts of ligand decomposition and heavies formation (all other factors being constant). In one embodiment, reactor temperature, residence time, and/or rhodium concentration may be higher in the secondary reactor to improve overall plant conversion, but since only a small portion of the total reaction fluid is being exposed to these harsher conditions, the overall plant ligand decomposition and/or heavies formation will be less than the situation where a full-sized reactor is operated under the same conditions to get the same olefin conversion.

The process of the invention employs a common product-catalyst separation zone, i.e., the effluent from both the primary and secondary reactors are sent to a shared product-catalyst separation zone in which the effluent is separated into at least one stream comprising primarily product, i.e., the crude product stream, and at least one stream comprising the relative majority of the catalyst in solution, i.e., the catalyst recycle stream. The crude product stream also contains substantial amounts of unreacted starting materials such as olefin and syngas.

The crude product stream is separated into an unrefined product stream and an unreacted starting materials stream. These unreacted starting materials are sent to the secondary reactor. The unrefined product stream advantageously is sent for further processing, e.g., refining or hydrogenation to alcohols. In many cases, the unrefined product stream may still retain some unreacted olefin which can be optionally recovered by syngas stripping, distillation, flashing, or using a stabilizer system, such as that disclosed in Example 5 of U.S. Pat. No. 4,827,042, and recycled back to the process. These operations advantageously occur after the primary product-catalyst separation zone. The catalyst recycle stream is recycled back to the reactors. In one embodiment of the invention, one catalyst recycle stream exits the separation zone and is split, then the split streams are recycled to the primary and secondary reactors. For the purposes of the invention, the term "product-catalyst separation zone" means any means to separate a substantial portion of the aldehyde product from a mixture of product and catalyst solution. Advantageously, more than 90% and more preferably, more than 95% of the total product is separated from the catalyst in the product-catalyst separation zone, although relatively small portions of product may also be collected by other equipment, such as vent knockout pots and the like.

Any suitable technique for separating the product from the reactor effluents can be employed. Unit operations suitable for use in the product-catalyst separation zone are well known to those skilled in the art and can comprise, for example, solvent extraction, membrane separation, crystallization, phase separation or decanting, filtration, distillation, and the like, or any combination thereof. Examples of distillation include flashing, wiped film evaporation, falling film evaporation, gas stripping, and distillation in any other type of conventional distillation equipment. Examples of membrane separation processes are disclosed in U.S. Pat. Nos. 5,430,194 and 5,681,473. For the purposes of the invention, the term "vaporization" will be used to encompass these unit operations, and the term "vaporizer" is used synonymously with "product-catalyst separation zone."

The preferred and conventional method of product-catalyst separation is distillation, preferably in a falling-film evaporator, in one or more stages under normal, reduced or elevated pressure, as appropriate, with the non-volatilized metal catalyst-containing residue being recycled to the reactors. For example, separation and catalyst recycle for a single train is described in U.S. Pat. No. 5,288,918, and the separation technique employed there can be employed in the process of the invention. Preferably, the liquid effluent of the primary reactor is fed to a vaporizer and the liquid effluent of the secondary reactor is fed to the same vaporizer. The non-vaporized, liquid effluent from the common vaporizer advantageously is split and recycled to the primary and secondary reactors.

The common vaporizer may comprise multiple vaporization units in series, such as high pressure and low pressure vaporizers, as shown, for example, in CN 102826969. For example, the primary reactor and secondary reactor each may have its own high pressure vaporizer, and each non-volatilized stream from the high pressure vaporizers is fed to the common low pressure vaporizer. This allows recycling of pressurized lights, such as propylene or butene, to each reactor from its own high pressure vaporizer, and the final product-catalyst separation is performed in the common low pressure vaporizer. In any case, the common final catalyst recycle stream is split, either at or after the vaporizer, and is sent back to the primary and secondary reactors.

As indicated above, the desired aldehydes may be recovered from the reaction mixture. For example, the recovery techniques disclosed in U.S. Pat. Nos. 4,166,773, 4,148,830 and 4,247,486 can be employed. In a continuous liquid catalyst recycle process, the portion of the liquid reaction mixture (containing aldehyde product, catalyst, etc.), i.e., reaction fluid, removed from the reactors can be passed to a product-catalyst separation zone, e.g., vaporizer/separator, wherein the desired aldehyde product can be separated via distillation, in one or more stages, under normal, reduced or elevated pressure, from the liquid reaction fluid, then condensed and collected in a product receiver, and further refined or purified if desired. The remaining non-volatilized catalyst containing liquid reaction mixture is recycled back to the reactors, as may any other volatile materials, e.g., unreacted olefin, together with any hydrogen and carbon monoxide after separation thereof from the condensed aldehyde product. In general, it is preferred to separate the desired aldehydes from the catalyst-containing reaction mixture under reduced pressure and at low temperatures so as to avoid possible degradation of the organophosphorous ligand and reaction products.

More particularly, distillation of the desired aldehyde product from the metal-organophosphorous complex catalyst containing reaction fluid may take place at any suitable temperature desired. In general, it is preferred that such distillation take place at relatively low temperatures, such as below 150° C., and more preferably at a temperature in the range of from 50° C. to 140° C. It is generally preferred that such aldehyde distillation take place under a total gas pressure that is lower than the total gas pressure employed during hydroformylation when low boiling aldehydes (e.g., $C_3$ to $C_6$) are involved, or under vacuum when high boiling aldehydes (e.g., $C_7$ or greater) are involved. In general, distillation pressures ranging from vacuum pressures up to a total gas pressure of 340 kPa (49.3 psia) are sufficient for most purposes.

The crude aldehyde product stream separated from the catalyst solution contains unreacted olefin and syngas. In one embodiment, the vaporized crude aldehyde is condensed to a liquid unrefined product stream and the non-condensed vapor consisting mostly of olefin and syngas are sent to the secondary reactor. In another embodiment, the crude product stream is refined, e.g., distilled, to generate a product-enriched stream and an olefin-enriched stream; and the former is sent for further processing, e.g., refining, and the latter is sent to the secondary reactor. For brevity, the olefin-enriched stream separated from the crude product stream will be termed the "vaporizer vent stream". The vaporizer vent stream from the vaporizer can be handled by conventional means such as, for example, sending it to a refining process if desired to enrich the olefin content further before sending to the secondary reactor.

In one embodiment, the catalyst recycle stream sent to the each reactor may be split between two or more different reaction zones within each reactor to control the N:I ratio within each reactor as taught in WO 2011/087690. This also reduces the average residence time of the catalyst at elevated temperature, thereby reducing heavies formation and ligand decomposition.

The recycle procedure generally involves withdrawing a portion of the liquid reaction medium containing the catalyst and aldehyde product from at least one of the hydroformylation reactors, either continuously or intermittently, and recovering the aldehyde product therefrom by use of a product-catalyst separation zone. Collection of the removed aldehyde product, typically by condensation of the volatilized materials, and separation and further refining thereof, e.g., by distillation, can be carried out in any conventional manner, and the crude aldehyde product can be passed on for further purification and isomer separation, if desired, and any recovered reactants, e.g., olefinic starting material and syngas, can be recycled in any desired manner to the hydroformylation zone (reactor). The aldehyde products can be refined by distillation, including multi-step distillation, to remove unreacted material and recover a purified product. The recovered metal catalyst-containing raffinate of such separation or recovered non-volatilized metal catalyst-containing residue of such separation can be recycled, to one or more of the hydroformylation reactors as described above.

Various types of recycle procedures are known in the art and may involve the liquid recycling of the metal-organophosphorous complex catalyst fluid separated from the desired aldehyde reaction product(s), such as disclosed, for example, in U.S. Pat. No. 4,148. A continuous liquid catalyst recycle process is preferred. Examples of suitable liquid catalyst recycle procedures are disclosed in U.S. Pat. Nos. 4,668,651; 4,774,361; 5,102,505, 5,110,990, 5,952,530 and 8,134,031.

The resulting product stream can be processed by conventional means. For example, the aldehyde products can be separated and separately processed by hydrogenation or aldolisation/hydrogenation to alcohols. Alternatively, the aldehyde products are not separated but are processed together. For example, the aldehyde mixture can be hydrogenated and the individual alcohols can be separated after hydrogenation. Another possibility involves aldolization/hydrogenation to a mixture of alcohols and higher alcohols followed by distillation to isolate the individual alcohols. An example of such multiple processing schemes is given in WO 2012/008717.

The use of an extractor, mentioned above, may introduce various levels of water to the catalyst recycle streams and thereby, to the reactors. As taught in WO 2012/064586 and JP 2006/306815, the presence of water in the hydroformylation reactors may be important to mitigate reactor fouling. A primary source of this water is from the extractor, and a primary means to remove water is via a vaporizer. Changes in the catalyst recycle rate will necessarily change the amount of water being delivered to each reactor and it may be desirable to have auxiliary means to add water to some or all reactors independently of the catalyst treatment processes. Alternatively, it may be desirable to keep one reactor "dry" to mitigate ligand hydrolysis, as taught in U.S. Pat. No. 7,262,330. Thus only treating one catalyst recycle stream may be desirable in order to remove the degradation acids from the more tolerant reactor. A buffer treatment zone, if employed, may be a single vessel or may comprise two or more discreet vessels.

Illustrative non-optically active aldehyde products include e.g., propionaldehyde, n-butyraldehyde, isobutyraldehyde, n-valeraldehyde, 2-methyl 1-butyraldehyde, hexanal, hydroxyhexanal, 2-methyl valeraldehyde, heptanal, 2-methyl 1-hexanal, octanal, 2-methyl 1-heptanal, nonanal, 2-methyl-1-octanal, 2-ethyl 1-heptanal, 3-propyl 1-hexanal, decanal, adipaldehyde, 2-methylglutaraldehyde, 2-methyladipaldehyde, 3-methyladipaldehyde, 3-hydroxypropionaldehyde, 6-hydroxyhexanal, alkenals, e.g., 2-, 3- and 4-pentenal, alkyl 5-formylvalerate, 2-methyl-1-nonanal, undecanal, 2-methyl 1-decanal, dodecanal, 2-methyl 1-undecanal, tridecanal, 2-methyl 1-tridecanal, 2-ethyl, 1-dodecanal, 3-propyl-1-undecanal, pentadecanal, 2-methyl-1-tetradecanal, hexadecanal, 2-methyl-1-pentadecanal, heptadecanal, 2-methyl-1-hexadecanal, octadecanal, 2-methyl-1-heptadecanal, nonodecanal, 2-methyl-1-octadecanal, 2-ethyl 1-heptadecanal, 3-propyl-1-hexadecanal, eicosanal, 2-methyl-1-nonadecanal, heneicosanal, 2-methyl-1-eicosanal, tricosanal, 2-methyl-1-docosanal, tetracosanal, 2-methyl-1-tricosanal, pentacosanal, 2-methyl-1-tetracosanal, 2-ethyl 1-tricosanal, 3-propyl-1-docosanal, heptacosanal, 2-methyl-1-octacosanal, nonacosanal, 2-methyl-1-octacosanal, hentriacontanal, 2-methyl-1-triacontanal, and the like.

Illustrative optically active aldehyde products include (enantiomeric) aldehyde compounds prepared by the asymmetric hydroformylation process of this invention such as, e.g., S-2-(p-isobutylphenyl)-propionaldehyde, S-2-(6-methoxy-2-naphthyl)propionaldehyde, S-2-(3-benzoylphenyl)-propionaldehyde, S-2-(p-thienoylphenyl)propionaldehyde, S-2-(3-fluoro-4-phenyl)phenylpropionaldehyde, S-2-[4-(1,3-dihydro-1-oxo-2H-isoindol-2-yl)phenyl] propionaldehyde, and S-2-(2-methylacetaldehyde)-5-benzoylthiophene.

Figure 2:
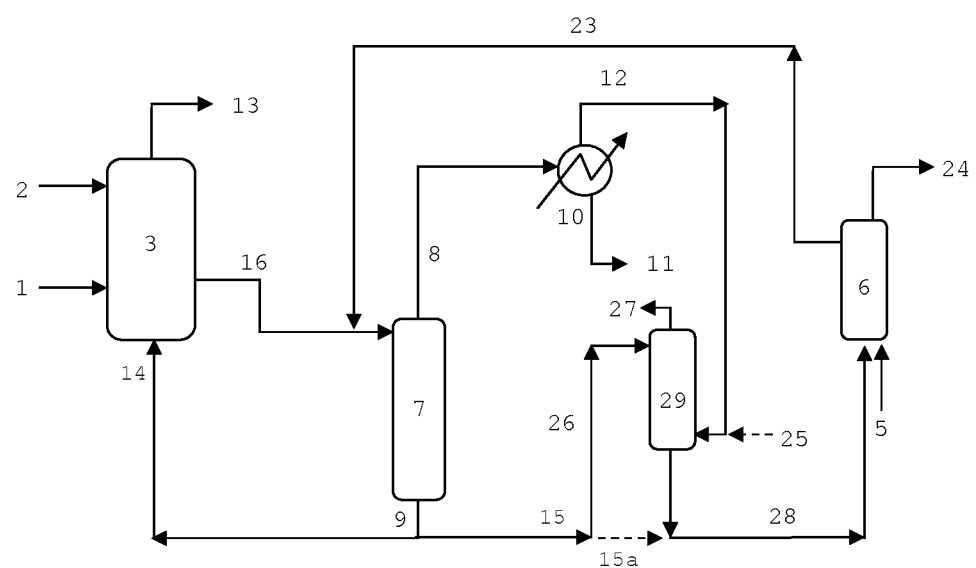
FIG. 2 is a schematic of an hydroformylation process that employs a common product-catalyst separation zone, e.g. a vaporizer.

Various embodiments of the process are shown in FIGS. 1 and 2.

Referring to FIG. 1, the olefin (e.g., propylene) (1) and syngas (2) are fed to the primary reactor represented by reactor (3). The effluent of reactor (3) is fed, via line (16), to the separation zone (7), represented here by a vaporizer, in which a crude product stream (8) is separated from a catalyst recycle stream (9). Stream (8) is condensed by condenser (10) to obtain unrefined aldehyde products (11) which are then further processed by conventional means, such as being treated with a syngas stripping tower to recover starting material (U.S. Pat. No. 5,087,763) or refining by conventional means such as distillation. The vaporizer vent stream (12) is then compressed via compressor (22) and sent to the secondary reactor, represented by secondary reactor (6) with makeup syngas (5) as needed. The effluent of secondary reactor (6) is sent via line (23) back to the separation zone (7). Vent (24) is a vapor purge to remove inerts such as propane, $N_2$, $CO_2$, and the like, and may be present at the top of the reactor or, preferably, in a flashpot on stream (23). Optionally, stream (25) may be other vents from reactors, stabilizers, storage tanks, etc.

The unrefined product stream (11) may be sent to an optional syngas stripping tower (not shown) and/or an optional stabilizer column (30) prior to being stored or processed further as stream (11a). The primary reactor may have an optional vent (13), and portions of the vent may be recycled as desired. For example, part or all of vents (13) or (13a) may also be sent via line (25) to compressor (22) and then to secondary reactor (6). The primary and/or secondary reactor may comprise multiple reactors in parallel or series, but additional reactors are not shown for the sake of simplicity. Lines (16) and (23) may combine before or inside the separation zone.

Recycle stream (9) comprising catalyst, excess ligand, solvent (usually aldehyde heavies), residual aldehyde products, and unreacted reactants is returned to the primary and secondary reactors via streams (14) and (15), respectively.

Referring to FIG. 2, which is essentially the same as FIG. 1 except that the vaporizer vent stream (12) is routed through a counter-current extraction zone (29), such as described in U.S. Pat. No. 5,001,274, wherein a portion of vaporizer tails stream (15) is diverted to the top of (29). This portion, stream (26), acts to absorb a substantial portion of the gaseous, unreacted olefin into the liquid phase and the combined streams (15a) and (26), now stream (28), continues to the secondary reactor (6). Unabsorbed gases (typically inerts, such as $N_2$, $CO_2$, $CH_4$, and syngas) leave (29) via vaporizer vent (27). Although not shown here, stream (26) may be further cooled prior to entry into (29). A small pump in stream (28) to deliver the liquid to reactor (6) under pressure is generally required but is less expensive than the compressor used in FIG. 1. Optional stream (15a) is the portion of stream (15) not sent to (29) and is present to allow operational flexibility during startups, for example.

SPECIFIC EMBODIMENTS OF THE INVENTION

All parts and percentages in the following examples are by weight unless otherwise indicated. Pressures are given as absolute pressure unless otherwise indicated.

COMPARATIVE EXPERIMENT A

Figure 3:
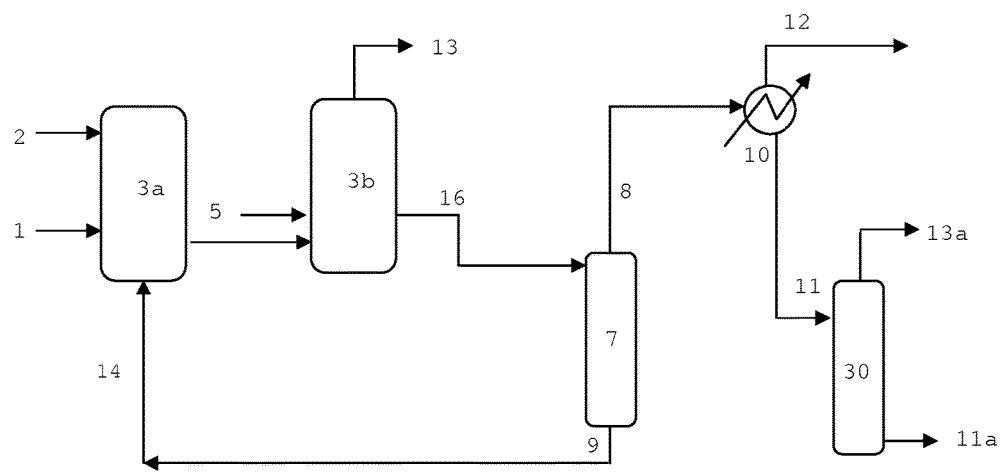
FIG. 3 is a schematic of an hydroformylation process of Comparative Experiment A.

A conventional Oxo reaction system with two identical continuously stirred tank reactors (CSTR) as depicted in FIG. 3 is modeled using ASPEN Plus Dynamics™ process simulation software. The catalyst is a typical Rh-bisphosphite catalyst as described in U.S. Pat. No. 4,668,651 and the reaction conditions are essentially those of Example 9 of that patent for propylene (polymer grade, 99.5%) except that the initial target rhodium concentration for the first reactor is 80 ppm Rh. The Ligand:Rh ratio is >1. The vent from the stabilizer column (13a) is not recycled due to the low levels of contained propylene and lack of a compressor. Selected process conditions and the rate of unrefined aldehyde production are shown in Table 1 based on a olefin feed rate of 19585 kg/hr of polymer-grade propylene.

EXAMPLES 1-4

An Oxo reaction system of the invention as depicted in FIG. 1 is modeled using ASPEN Plus Dynamics™ process simulation software. The reaction conditions are those of C.E. A, but the process configuration is different. The system comprises a primary CSTR (R1), having the same volume as a CSTR of C.E. A, and a smaller, secondary CSTR (R2). A vent stream from the stabilizer column (13a) is fed via line (25) to the compressor (22).

The basis for the modeling the reactor control system is as follows:

1) The Oxo reaction rate is directly proportional to rhodium concentration at constant temperature
2) Rhodium concentration in each reactor is a function of the recycle catalyst mass flow rate and recycle rhodium concentration fed to each reaction. The liquid volume in each reactor is constant.
3) The effects of items 1 and 2 combine so the oxo reaction rate is a function of the recycle catalyst feed rate and recycle catalyst rhodium concentration.
4) Since propylene Oxo reaction kinetics are more responsive to changes in the kinetic variables then the raffinate kinetics, the control scheme is designed to control the primary reactor rhodium concentration, and to keep the temperature of reactor (3) constant, and let the rhodium concentration in the secondary reactor vary as necessary. The secondary reactor temperature can be reduced to offset any higher than design rhodium concentrations.

5) Variation in temperature due to changes in the rhodium concentration caused by changes in the recycle flow are slow, on the order of hours. Therefore, reactor temperature control is done using conventional cooling techniques such as internal cooling coils, external heat exchangers or both.

Selected process conditions and the rate of unrefined aldehyde production are shown in Table 1.

TABLE 1

|  | C.E. A | Example 1 | Example 2 | Example 3 | Example 4 |
|---|---|---|---|---|---|
| R2/R1 Volume | 100% | 20% | 20% | 20% | 20% |
| R1 PPM Rh | 80 | 80 | 80 | 80 | 80 |
| % Catalyst recycle to R2 | 100% | 10.0% | 11.5% | 11.3% | 17.5% |
| Propylene Grade | Polymer | Polymer | Polymer | Polymer | Polymer |
| R1 Liq Vol $m^3$ | 148.5 | 148.5 | 148.5 | 148.5 | 148.5 |
| R1 Temperature C. | 70.0 | 70.0 | 70.0 | 70.0 | 70.0 |
| R1 Rh ppm | 80 | 80 | 80 | 80 | 80 |
| R1 Density $kg/m^3$ | 703.7 | 704.0 | 704.0 | 704.0 | 704.0 |
| R1 Mass kg | 104,505.7 | 104,549.3 | 104,549.5 | 104,548.3 | 104,549.9 |
| R1 Rh kg | 8.4 | 8.4 | 8.4 | 8.4 | 8.4 |
| R2 Liq Vol $m^3$ | 148.5 | 29.7 | 29.7 | 29.7 | 29.7 |
| R2 Temperature C. | 70.0 | 70.0 | 70.0 | 85.0 | 70.0 |
| R2 Rh ppm | 78 | 71 | 78 | 78 | 100 |
| R2 Density $kg/m^3$ | 717.5 | 704.4 | 706.6 | 693.9 | 704.4 |
| R2 Mass kg | 106,554.2 | 20,921.3 | 20,984.9 | 20,608.4 | 20,921.3 |
| R2 Rh kg | 8.3 | 1.5 | 1.6 | 1.6 | 2.1 |
| Total Rh kg | 16.7 | 9.8 | 10.0 | 10.0 | 10.5 |
| R2 Vent Rate (13) kg/hr | 587 | N/A | N/A | N/A | N/A |
| R2 Vent Rate (24) kg/hr | N/A | 1,498 | 1,462 | 1,306 | 1,386 |
| Vaporizer Vent Rate (12) kg/hr | 608 | N/A | N/A | N/A | N/A |
| Stabilizer Vent Rate (13a) kg/hr | 356 | N/A | N/A | N/A | N/A |
| Total Vent Rate kg/hr | 1,551 | 1,498 | 1,462 | 1,306 | 1,386 |
| Stabilizer Vent Recycle (25) kg/hr | N/A | 770 | 770 | 766 | 772 |
| R2 Residence Time hr | 2.4 | 4.5 | 4.3 | 4.3 | 3.6 |
| Unrefined Aldehyde Product kg/hr | 32,409 | 32,482 | 32,519 | 32,670 | 32,594 |
| Propylene Conversion % | 96.4% | 96.6% | 96.7% | 97.1% | 96.9% |

The initial catalyst and Ligand:Rh ratios provide high reaction rates, high conversions, and low ligand consumption at design rates for C.E. A as well as for Example 1. The propylene conversion to product can readily be assessed by the amount of unrefined aldehyde produced. The results surprisingly demonstrate that the process of the invention, using a much smaller R2, achieves equal or superior conversion from a constant feed level compared to the process of C.E. A.

The results for Example 1 demonstrate conversion and efficiency for the process of the invention that are comparable to those for a process running 2 large reactors in series. The improved design saves nearly 7 kg of rhodium inventory (16.7 kg-9.8 kg), which is a 41% reduction, and has a 40% reduced initial ligand charge compared to the comparative process. The process of the invention allows good control of the rhodium concentration profile. This results in good raw material efficiencies and good control of reactor temperature.

Examples 2-4 demonstrate that higher rhodium concentration, temperature, or both can be used to increase the conversion. Since only 20% of the reaction volume is under these harsh conditions, substantially less ligand decomposition and heavies formation would be expected to occur compared to C.E.A operating under the same conditions. Even at the elevated rhodium concentration in R2 in Ex 4, the total amount of rhodium is still 37% less than that of C.E. A.

EXAMPLES 5-8 AND COMPARATIVE EXPERIMENT B

The procedures of Example 1-4 and Comparative Experiment A are repeated except that chemical grade propylene (95% propylene) is fed at a rate of 20655 kg/hr. The results are given in the following table.

TABLE 2

|  | C.E. B | Example 5 | Example 6 | Example 7 | Example 8 |
|---|---|---|---|---|---|
| R2/R1 Volume | 100% | 20% | 20% | 20% | 20% |
| R1 PPM Rh | 80 | 80 | 80 | 80 | 80 |
| % Catalyst recycle to R2 | 100% | 10.0% | 13.8% | 13.0% | 21.0% |
| Propylene Grade | Chemical | Chemical | Chemical | Chemical | Chemical |
| R1 Liq Vol m$^3$ | 148.5 | 148.5 | 148.5 | 148.5 | 148.5 |
| R1 Temperature C. | 70.0 | 70.0 | 70.0 | 70.0 | 70.0 |
| R1 Rh ppm | 80 | 80 | 80 | 80 | 80 |
| R1 Density kg/m$^3$ | 696.4 | 696.4 | 696.4 | 696.3 | 696.3 |
| R1 Mass kg | 103,411.1 | 103,408.0 | 103,408.0 | 103,407.8 | 103,407.8 |
| R1 Rh kg | 8.3 | 8.3 | 8.3 | 8.3 | 8.3 |
| R2 Liq Vol m$^3$ | 148.5 | 29.7 | 29.7 | 29.7 | 29.7 |
| R2 Temperature C. | 70.0 | 70.0 | 70.0 | 85.0 | 70.0 |
| R2 Rh ppm | 78 | 63 | 78 | 78 | 100 |
| R2 Density kg/m$^3$ | 710.3 | 685.3 | 689.0 | 678.6 | 696.7 |
| R2 Mass kg | 105,473.6 | 20,354.4 | 20,464.1 | 20,153.9 | 20,692.0 |
| R2 Rh kg | 8.2 | 1.3 | 1.6 | 1.6 | 2.1 |
| Total Rh kg | 16.5 | 9.6 | 9.9 | 9.8 | 10.3 |
| R2 Vent Rate (13) kg/hr | 648 | N/A | N/A | N/A | N/A |
| R2 Vent Rate (24) kg/hr | N/A | 2,602 | 2,502 | 2,329 | 2,417 |
| Vaporizer Vent Rate (12) kg/hr | 1,296 | N/A | N/A | N/A | N/A |
| Stabilizer Vent Rate (13a) kg/hr | 618 | N/A | N/A | N/A | N/A |
| Total Vent Rate kg/hr | 2,562 | 2,602 | 2,502 | 2,329 | 2,417 |
| R2 Liquid Out kg/hr | 44,427 | 5,227 | 5,845 | 5,546 | 6,975 |
| Stabilizer Vent Recycle (25) kg/hr | N/A | 860 | 864 | 863 | 867 |
| R2 Residence Time hr | 2.4 | 3.9 | 3.5 | 3.6 | 3.0 |
| Unrefined Aldehyde Product kg/hr | 32,474 | 32,454 | 32,554 | 32,722 | 32,639 |
| Propylene Conversion % | 96.1% | 96.0% | 96.3% | 96.8% | 96.6% |

Despite the higher levels of inerts in the feed, the rate of unrefined aldehyde production of the process of Examples 5-8 is still surprisingly substantially equal to or greater than that of the conventional design represented by C.E. B. Propane buildup to unacceptable levels surprisingly is not observed since vent (24) is sufficient to purge inerts while maintaining comparable overall conversion.

The invention offers the following advantages:
1) Significantly smaller reactor volume is needed to achieve the same conversion at the same temperature and catalyst concentration. Since ligand usage is, in part, a function of reactor volume and since less ligand is present, the overall ligand usage is significantly reduced. Many commercial ligands are quite expensive and this gives a substantial variable cost savings.
2) Similarly, a smaller total reaction volume means less rhodium is needed, which provides a substantial cost reduction.
3) The heavies formation rate is reduced due to the smaller reaction volume.
4) Smaller reactors are generally less expensive.
5) The process allows good control of rhodium concentration and operating temperatures, resulting in minimized ligand consumption and heavies formation.

What is claimed is:

1. A process comprising:
   (a) contacting in a primary reactor CO, $H_2$, and a feed stream comprising an olefin in the presence of a hydroformylation catalyst in a reaction fluid under hydroformylation conditions sufficient to form at least one aldehyde product;
   (b) passing a liquid effluent stream from the primary reactor to a product-catalyst separation zone;
   (c) removing from the product-catalyst separation zone a crude product stream and a liquid catalyst recycle stream;
   (d) then, separating the crude product stream into a vent stream and an unrefined product stream;
   (e) passing the vent stream, which comprises an olefin and syngas, to a secondary reactor;
   (f) contacting in the secondary reactor CO, $H_2$, and the olefin of the vent stream in the presence of a hydroformylation catalyst in a reaction fluid under hydroformylation conditions sufficient to form at least one aldehyde product;
   (g) passing a liquid effluent stream from the secondary reactor to the product-catalyst separation zone.

2. The process of claim 1 further comprising splitting the recycle stream into a first recycle stream and a second recycle stream, and sending the first recycle stream to at least partially to one reactor and sending the second recycle stream at least partially to another reactor.

3. The process of claim 1 wherein the volume of the secondary reactor is no more than 80% of the volume of the primary reactor.

4. The process of claim 1 wherein the volume of the secondary reactor is no more than 50% of the volume of the primary reactor.

5. The process of claim 1 wherein the volume of the secondary reactor is no more than 35% of the volume of the primary reactor.

6. The process of claim 1 wherein the volume of the secondary reactor is no more than 25% of the volume of the primary reactor.

7. The process of claim 1 wherein the concentration of catalytic metal in the primary reactor is controlled in response to measuring components within the catalyst recycle stream that correlate with the catalytic metal concentration.

8. The process of claim 1 wherein the separating in the common product-catalyst separation zone comprises vaporization.

9. The process of claim 1 wherein the feed stream comprising an olefin is a feed stream comprising an olefin and an alkane.

10. The process of claim 1 wherein the feed stream comprising an olefin is chemical grade propylene.

11. The process of claim 1 wherein the residence time in the secondary reactor is at least 20% longer than in the primary reactor.

12. The process of claim 1 wherein the catalyst comprises a hydrolyzable organophosphorous ligand.

13. The process of claim 2 wherein the first recycle stream is sent to the primary reactor and the second recycle stream is sent to the secondary reactor.

14. The process of claim 13 wherein the amount of the first recycle stream sent to the primary reactor is determined by inferential means based on observed reactor temperature, olefin and CO partial pressures, and total pressure to control the olefin partial pressure to within a desired range.

15. The process of any one of the preceding claims wherein the crude product stream comprises unreacted olefin and syngas.

* * * * *